United States Patent [19]
Brown et al.

[11] Patent Number: 6,166,022
[45] Date of Patent: Dec. 26, 2000

[54] COMPOUNDS

[75] Inventors: Roger Brown, Loughborough; Garry Pairaudeau, Stamford, both of United Kingdom

[73] Assignee: AstraZeneca UK Limited, London, United Kingdom

[21] Appl. No.: 09/155,567

[22] PCT Filed: Jul. 15, 1998

[86] PCT No.: PCT/SE98/01394

§ 371 Date: Sep. 30, 1998

§ 102(e) Date: Sep. 30, 1998

[87] PCT Pub. No.: WO99/05144

PCT Pub. Date: Feb. 4, 1999

[30] Foreign Application Priority Data

Jul. 22, 1997 [SE] Sweden .................................. 9702774

[51] Int. Cl.$^7$ ...................... C07D 487/04; C07D 249/00; C07D 239/00; A61K 31/505; A61K 31/41
[52] U.S. Cl. ........................................... 514/258; 544/254
[58] Field of Search .............................. 544/254; 514/258

[56] References Cited

U.S. PATENT DOCUMENTS 5,506,347  4/1996  Erion et al. .............................. 536/4.1

FOREIGN PATENT DOCUMENTS

| 0215759 | 3/1987 | European Pat. Off. . |
| 0368640 | 5/1990 | European Pat. Off. . |
| 9703084 | 1/1997 | WIPO . |

*Primary Examiner*—Mukund J. Shah
*Assistant Examiner*—Hong Liu
*Attorney, Agent, or Firm*—Nixon & Vanderhye

[57] ABSTRACT

Triazolo[4,5-d]pyrimidine compounds of the formula

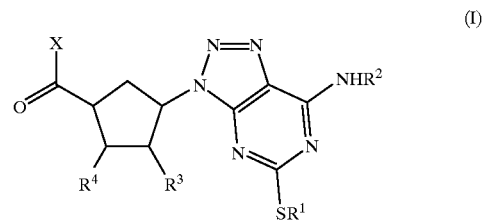

(I)

where $R^1$ through $R^4$ and X are as defined in the specification are provided, together with compositions containing them, a process for their preparation and methods of use. The compounds are useful in the treatment of platelet aggregation disorders and angina.

11 Claims, No Drawings

COMPOUNDS

The present invention provides new triazolo[4,5-d]pyrimidine compounds, their use as medicaments, compositions containing them and processes for their preparation.

Platelet adhesion and aggregation are initiating events in arterial thrombosis. Although the process of platelet adhesion to the sub-endothelial surface may have an important role to play in the repair of damaged vessel walls, the platelet aggregation that this initiates can precipitate acute thrombotic occlusion of vital vascular beds, leading to events with high morbidity such as myocardial infarction and unstable angina. The success of interventions used to prevent or alleviate these conditions, such as thrombolysis and angioplasty is also compromised by platelet mediated occlusion or re-occlusion.

A number of converging pathways lead to platelet aggregation. Whatever the initial stimulus, the final common event is a cross linking of platelets by binding of fibrinogen to a membrane binding site, glycoprotein IIb/IIIa (GPIIb/IIIa). The high anti-platelet efficacy of antibodies or antagonists for GPIIb/IIIa is explained by their interference with this final common event. However, this efficacy may also explain the bleeding problems that have been observed with this class of agent. Thrombin can produce platelet aggregation largely independently of other pathways but substantial quantities of thrombin are unlikely to be present without prior activation of platelets by other mechanisms. Thrombin inhibitors such as hirudin are highly effective anti-thrombotic agents, but again may produce excessive bleeding because they function as both anti-platelet and anti-coagulant agents (The TIMI 9a Investigators (1994), *Circulation* 90, pp. 1624–1630; The Global Use of Strategies to Open Occluded Coronary Arteries (GUSTO) IIa Investigators (1994) *Circulation* 90, pp. 1631–1637; Neuhaus K. L. et. al. (1994) *Circulation* 90, pp.1638–1642).

It has been found that ADP acts as a key mediator of thrombosis. A pivotal role for ADP is supported by the fact that other agents, such as adrenaline and 5-hydroxytryptamine (5HT, serotonin) will only produce aggregation in the presence of ADP. The limited anti-thrombotic efficacy of aspirin may reflect the fact that it blocks only one source of ADP which is that released in a thromboxane-dependent manner following platelet adhesion (see e.g. Antiplatelet Trialists' Collaboration (1994), *Br. Med. J.* 308, pp. 81–106; Antiplatelet Trialists' Collaboration (1994), *Br. Med. J.* 308, pp.159–168). Aspirin has no effect on aggregation produced by other sources of ADP, such as damaged cells or ADP released under conditions of turbulent blood flow. ADP-induced platelet aggregation is mediated by the $P_{2T}$-receptor subtype uniquely located on the platelet membrane. Recently it has been shown that antagonists at this receptor offer significant improvements over other anti-thrombotic agents. Accordingly there is a need to find $P_{2T}$-antagonists as anti-thrombotic agents.

It has now been found that a series of triazolo[4,5-d]pyrimidine derivatives are $P_{2T}$-antagonists. In a first aspect the invention therefore provides a compound of formula (I):

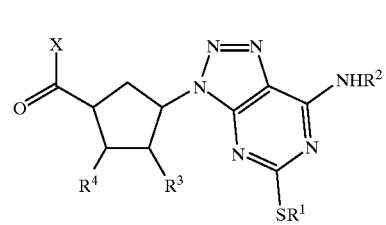

wherein:

$R^1$ is a $C_{1-6}$ alkyl, $C_{3-8}$-cycloalkyl or a phenyl group, each group being optionally substituted by one or more substituents selected from halogen, $OR^6$, $NR^7R^8$, $SR^9$ or $C_{1-6}$ alkyl (itself optionally substituted by one or more halogen atoms);

$R^2$ is $C_{1-8}$ alkyl optionally substituted by one or more substituents selected from halogen, $OR^6$, $NR^7R^8$, $SR^9$, $C_{3-8}$-cycloalkyl, aryl (optionally substituted by one or more alkyl groups and/or halogen atoms), or $C_{1-6}$-alkyl; or $R^2$ is a $C_{3-8}$-cycloalkyl group optionally substituted by one or more substituents selected from halogen, $OR^6$, $NR^7R^8$, $SR^9$, $C_{1-6}$-alkyl or phenyl (the latter two being optionally substituted by one or more substituents selected from halogen, $NO_2$, $C(O)R^6$, $OR^6$, $SR^9$, $NR^{10}R^{11}$, phenyl and $C_{1-6}$-alkyl which is optionally substituted by one or more halogen atoms);

one of $R^3$ or $R^4$ is hydrogen and the other is hydroxy;

X is OH or $NHR^5$;

$R^5$ is a $C_{1-6}$-alkyl group substituted by COOH or $C(O)NR^7R^8$ and optionally by one or more further substituents selected from halogen, $OR^{12}$, $C(NH)NR^{13}R^{14}$, $C(O)NR^{15}R^{16}$, phenyl (optionally substituted by one or more groups selected from halogen, $NO_2$, $C(O)R^6$, $OR^6$, $NR^7R^8$, $SR^9$ and $C_{1-6}$-alkyl) or $C_{1-6}$-alkyl (optionally substituted by one or more hydroxy or phenyl groups);

or $R^5$ is a lactam ring of formula (i):

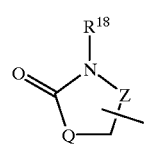

wherein Q is a $(CH_2)_m$ moiety where m is 1, 2 or 3, Z is O, C(O) or $CH_2$ and $R^{18}$ is hydrogen or $C_{1-6}$-alkyl;

$R^6$, $R^9$, $R^{12}$, $R^{13}$, $R^{14}$, $R^{15}$ and $R^{16}$ are independently hydrogen or $C_{1-6}$-alkyl;

$R^7$ and $R^8$ are independently hydrogen, $C_{1-6}$-alkyl (optionally substituted by one or more phenyl groups) or phenyl groups; and $R^{10}$ and $R^{11}$ are independently hydrogen, $C_{1-6}$-alkyl or acyl groups;

or a pharmaceutically acceptable salt or solvate thereof.

Alkyl groups, whether alone or as part of another group, can be straight chained or branched. Compounds of formula (I) are capable of existing in stereoisomeric forms including enantiomers and the invention extends to each of these stereoisomeric forms and to mixtures thereof including racemates. The invention also extends to any tautomeric forms and mixtures thereof.

Preferably the compound of formula (I) has the following stereochemistry:

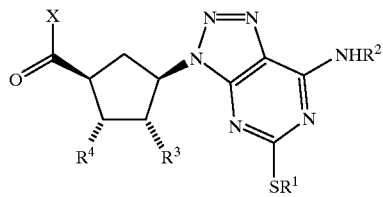

(I)

Suitably $R^1$ is a $C_{1-6}$ alkyl, $C_{3-8}$-cycloalkyl or a phenyl group, each group being optionally substituted by one or more substituents selected from halogen, $OR^6$, $NR^7R^8$, $SR^9$ or $C_{1-6}$ alkyl (itself optionally substituted by one or more halogen atoms). Preferably $R^1$ is $C_{1-6}$ alkyl or phenyl substituted by $C_{1-6}$ alkyl which is substituted by one or more fluorine atoms. More preferably $R^1$ is propyl or phenyl substituted by trifluomethyl.

Suitably $R^2$ is $C_{1-8}$ alkyl optionally substituted by one or more substituents selected from halogen, $OR^6$, $NR^7R^8$, $SR^9$, $C_{3-8}$-cycloalkyl, aryl (optionally substituted by one or more alkyl groups and/or halogen atoms), or $C_{1-6}$-alkyl; or $R^2$ is a $C_{3-8}$-cycloalkyl group optionally substituted by one or more substituents selected from halogen, $OR^6$, $NR^7R^8$, $SR^9$, $C_{1-6}$-alkyl or phenyl (the latter two being optionally substituted by one or more substituents selected from halogen, $NO_2$, $C(O)R^6$, $OR^6$, $SR^9$, $NR^{10}R^{11}$, phenyl and $C_{1-6}$-alkyl which is optionally substituted by one or more halogen atoms). Aryl groups include naphthyl and phenyl. Preferably $R^2$ is $C_{1-8}$ alkyl, in particular $C_{4-6}$ alkyl, or $C_{3-8}$-cycloalkyl optionally substituted by phenyl. More preferably $R^2$ is butyl or cyclopropyl optionally substituted by phenyl.

Suitably one of $R^3$ or $R^4$ is hydrogen and the other is hydroxy. Preferably $R^3$ is hydroxy and $R^4$ is hydrogen.

Suitably X is OH or $NHR^5$ where $R^5$ is a $C_{1-6}$-alkyl group substituted by COOH or $C(O)NR^7R^8$ and optionally by one or more further substituents selected from halogen, $OR^{12}$, $C(NH)NR^{13}R^{14}$, $C(O)NR^{15}R^{16}$, phenyl (optionally substituted by one or more groups selected from halogen, $NO_2$, $C(O)R^6$, $OR^6$, $NR^7R^8$, $SR^9$ and $C_{1-6}$-alkyl) or $C_{1-6}$-alkyl (optionally substituted by one or more hydroxy or phenyl groups or $R^5$ is a lactam ring of formula (i). Acyl groups include $C(O)C_{1-6}$-alkyl. Preferably X is OH or $NHR^5$ where $R^5$ is $C_{1-6}$-alkyl substituted by COOH and optionally further substituted by $C_{1-6}$-alkyl substituted by OH. More preferably X is OH or $NHR^5$ where $R^5$ is $CH_2COOH$ or $CH(CH_2OH)CO_2H$.

Particularly preferred compounds of the invention include:

[1S-(1α,3α,4β)]-3-[7-(Butylamino)-5-(propylthio)-3H-1,2,3-triazolo[4,5-d]pyrimidin-3-yl]-4-hydroxy-cyclopentanecarboxylic acid,

[1S-(1α,3α,4β)]-3-[7-(Butylamino)-5-[[4-(trifluoromethyl)phenyl]thio]-3H-1,2,3-triazolo[4,5-d]pyrimidin-3-yl]-4-hydroxy-cyclopentanecarboxylic acid, N-[(1S,3R,4S)-3-[7-(Butylamino)-5-[[4-(trifluoromethyl)phenyl]thio]-3H-1,2,3-triazolo[4,5-d]pyrimidin-3-yl]-4-hydroxy-cyclopentylcarbonyl]-L-serine, N-[(1S,3R,4S)-3-[7-(Butylamino)-5-[[4-(trifluoromethyl)phenyl]thio]-3H-1,2,3-triazolo[4,5-d]pyrimidin-3-yl]-4-hydroxy-cyclopentylcarbonyl]glycine,

[1S-[1α,3β,4α(1S*,2R*)]]-3-Hydroxy-4-[7-[(2-phenylcyclopropyl)amino]-5-(propylthio)-3H-1,2,3-triazolo[4,5-d]pyrimidin-3-yl]-cyclopentanecarboxylic acid, N-[(1S,3R,4S)-3-[7-(Butylamino)-5-(propylthio)-3H-1,2,3-triazolo[4,5-d]pyrimidin-3-yl]-4-hydroxy-cyclopentylcarbonyl]glycine,

[1S-(1α,3α,4β)]-3-[7-(Hexylamino)-5-(propylthio)-3H-1,2,3-triazolo[4,5-d]pyrimidin-3-yl]-4-hydroxy-cyclopentanecarboxylic acid,

[1S-(1α,2β,4α)]-4-[7-(Butylamino)-5-(propylthio)-3H-1,2,3-triazolo[4,5d]pyrimidin-3-yl]-2-hydroxy-cyclopentanecarboxylic acid, and pharmaceutically acceptable salts thereof.

According to the invention there is further provided a process for the preparation of a compound of formula (I) which comprises oxidising a compound of formula (II):

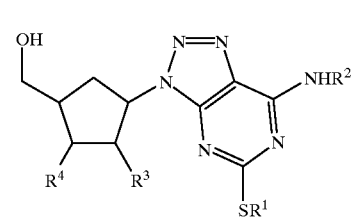

(II)

where $R^1$, $R^2$, $R^3$ and $R^4$ are as defined in formula (I) or are protected derivatives thereof, and optionally thereafter in any order:

converting a compound of formula (I) into a further compound of formula (I)

removing any protecting groups forming a pharmaceutically acceptable salt or solvate.

Compounds of formula (II) can be oxidised using known reagents such as pyridinium dichromate or chromium (VI) oxide Compounds of formula (II) where $R^3$ is hydroxy and $R^4$ is hydrogen can be prepared by dehalogenating compounds of formula (IV):

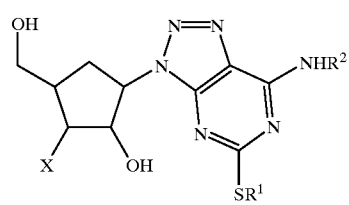

(IV)

where $R^1$ and $R^2$ are as defined in formula (II) and X is halogen. Preferably X is bromo. The reaction can be carried out using known reagents such as tributyltin hydride. The hydroxy groups in compounds of formula (IV) can be protected if necessary.

Compounds of formula (IV) can be prepared from the corresponding epoxide of formula (V):

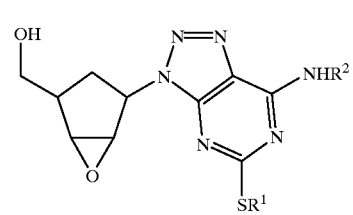

(V)

where $R^1$ and $R^2$ are as defined in formula (II) by treating with HCl or HBr. Compounds of formula (V) can be prepared from the corresponding diol, for example by treating the diol with 2-acetoxy-2-methylpropionyl bromide, followed by a base such as Amberlite® hydroxide resin.

Compounds of formula (II) where $R^3$ is hydrogen and $R^4$ is hydroxy can be prepared by dehydroxylating compounds of formula (VI):

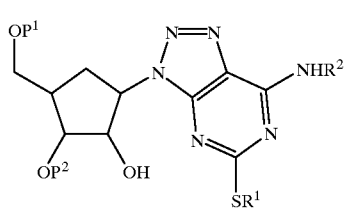

(VI)

where $R^1$ and $R^2$ are as defined in formula (II) and $P^1$ and $P^2$ are suitable protecting groups. The reaction can be carried out using treating compounds of formula (VI) with 1,1'-thiocarbonyldiimidazole followed by a trialkyltin hydride.

Compounds of formula (VI) are prepared by selective protection of the corresponding triols of formula (VII):

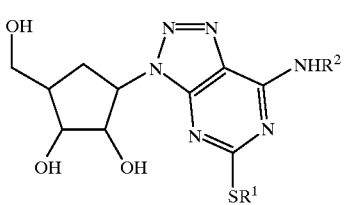

(VII)

where $R^1$ and $R^2$ are as defined in formula (II). Suitable reagents include 1,3-dichloro-1,1',3,3'-tetraisopropyldisiloxane.

A compound of formula (VII) can be prepared by reacting a compound of formula (VIII):

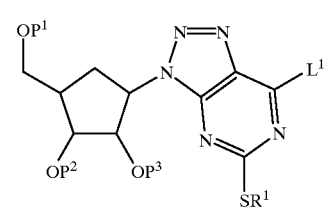

(VIII)

wherein $R^1$ is as defined in formula (I), $P^1$, $P^2$ and $P^3$ are hydrogen or are the same or different protecting groups, $L^1$ is a leaving group, for example a halogen atom, with $NH_2R^2$ or a salt of $NH_2R^2$ wherein $R^2$ is as defined above, in the presence of a base. Suitable salts of $NH_2R^2$ include hydrochlorides. Suitable bases include tertiary organic bases such as triethylamine or an inorganic base such as potassium carbonate.

A compound of formula (VIII) can be prepared by diazotising a compound of formula (IX):

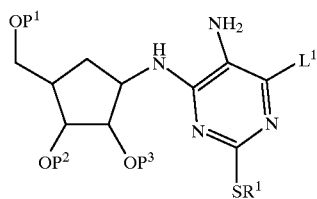

(IX)

wherein $R^1$, $L^1$, $P^1$, $P^2$ and $P^3$ are as defined above, with a metal nitrite, for example an alkali metal nitrite, especially sodium nitrite in dilute aqueous acid, for example 2M HCl, or with a $C_{1-6}$-alkyl nitrite in an inert solvent, at a temperature of from −20 to 100° C.; preferred conditions are isoamyl nitrite in acetonitrile at 80° C.

A compound of formula (IX) wherein $P^1$ is OH can be prepared by reducing a compound of formula (X):

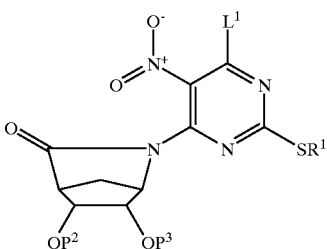

(X)

wherein $R^1$, $L^1$, $P^2$ and $P^3$ are as defined above. The reduction of the nitro group can be carried out for example by using hydrogenation with a transition metal catalyst at a temperature around room temperature, for example palladium on charcoal under an atmosphere of hydrogen, preferably at a pressure from 1 to 5 atmospheres, in a solvent, for example ethanol, or by using iron in an acidic solvent such as acetic acid at a temperature of about 100° C.

Reduction of the lactam can be carried out using complex metal hydrides such as lithium aluminium hydride in a solvent such as ether or preferably using sodium borohydride in a suitable solvent such as methanol.

A compound of formula (X) can be prepared by reacting a compound of formula (XI):

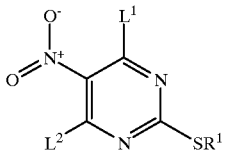

(XI)

wherein $L^1$ and $R^1$ are as defined above and $L^2$ is a leaving group, for example a halogen atom wherein $L^1$ and $L^2$ are preferably the same, with a compound of formula (XII):

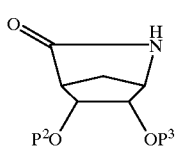

(XII)

wherein $P^2$ and $P^3$ are as defined above, in the presence of a base such as $C_{1-6}$-alkyl-M or MH wherein M is a metal ion, for example butyl lithium, in an inert solvent, such as tetrahydrofuran (THF), at a temperature of from −10 to 100° C. Preferably sodium hydride is used in THF at room temperature.

Preferably the compound of formula (XII) has the following stereochemistry such that the reaction schemes outlined above produce a compound having the stereochemistry of formula (Ia):

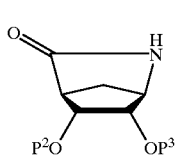

(XIIa)

Protecting groups can be added and removed using known reaction conditions. The use of protecting groups is fully described in 'Protective Groups in Organic Chemistry', edited by J W F McOmie, Plenum Press (1973), and 'Protective Groups in Organic Synthesis', 2nd edition, T W Greene & P G M Wutz, Wiley-Interscience (1991).

Ester protecting groups can be removed by basic hydrolysis, for example by using a metal hydroxide, preferably an alkali metal hydroxide, such as sodium hydroxide or lithium hydroxide, or quaternary ammonium hydroxide in a solvent, such as aqueous ethanol or aqueous tetrahydrofuran, at a temperature of from 10° to 100° C., preferably the temperature is around room temperature; or by acidic hydrolysis using a mineral acid such as HCl or a strong organic acid such as trichloroacetic acid in a solvent such as aqueous 1,4-dioxane. Trialkylsilyl protecting groups can be removed by the use of, for example, a fluoride ion source, for example tetra-n-butylammonium fluoride or hydrogen fluoride;

Benzyl groups can be removed by hydrogenolysis using a transition metal catalyst, for example palladium on charcoal, under an atmosphere of hydrogen, at a pressure of from 1 to 5 bar, in a solvent, such as acetic acid.

Salts of the compounds of formula (I) may be formed by reacting the free acid, or a salt thereof, or the free base, or a salt or a derivative thereof, with one or more equivalents of the appropriate base (for example ammonium hydroxide optionally substituted by $C_{1-6}$-alkyl or an alkali metal or alkaline earth metal hydroxide) or acid (for example a hydrohalic (especially HCl), sulphuric, oxalic or phosphoric acid). The reaction may be carried out in a solvent or medium in which the salt is insoluble or in a solvent in which the salt is soluble, e.g. water, ethanol, THF or diethyl ether, which may be removed in vacuo, or by freeze drying. The reaction may also be a metathetical process or it may be carried out on an ion exchange resin. The non-toxic physiologically acceptable salts are preferred, although other salts may be useful, e.g. in isolating or purifying the product.

Compounds of formula (I) can be converted into further compounds of formula (I) using standard chemistry. For example compounds of formula (I) where X is $NHR^5$ can be prepared from compounds of formula (I) where X is OH using coupling chemistry, for example in the presence of a coupling agent using methods known from peptide synthesis (see M. Bodanszky and A. Bodanszky, The Practice of Peptide Synthesis, Springer-Verlag, 1984). Suitable coupling agents include 1,1'-carbonyldiimidazole and dicyclohexylcarbodiimide; the preferred coupling agent is bromo-tris-pyrrolidino-phosphonium hexafluorophosphate, used in the presence of N,N-diethylisopropylamine. The reaction is preferably carried out in N,N-dimethylformamide (DMF) or tetrahydrofuran (THF) and preferably at a temperature of from −15° to 120° C., more preferably at a temperature of from 0° C. to room temperature.

All novel intermediates form a further aspect of the invention.

The compounds of the invention act as $P_{2T}$ receptor antagonists. Accordingly, the compounds are useful in therapy, especially adjunctive therapy, particularly they are indicated for use as: inhibitors of platelet activation, aggregation and degranulation, promoters of platelet disaggregation, anti-thrombotic agents or in the treatment or prophylaxis of unstable angina, coronary angioplasty (PTCA), myocardial infarction, perithrombolysis, primary arterial thrombotic complications of atherosclerosis such as thrombotic or embolic stroke, transient ischaemic attacks, peripheral vascular disease, myocardial infarction with or without thrombolysis, arterial complications due to interventions in atherosclerotic disease such as angioplasty, endarterectomy, stent placement, coronary and other vascular graft surgery, thrombotic complications of surgical or mechanical damage such as tissue salvage following accidental or surgical trauma, reconstructive surgery including skin and muscle flaps, conditions with a diffuse thrombotic/platelet consumption component such as disseminated intravascular coagulation, thrombotic thrombocytopaenic purpura, haemolytic uraemic syndrome, thrombotic complications of septicaemia, adult respiratory distress syndrome, anti-phospholipid syndrome, heparin-induced thrombocytopaenia and pre-eclampsia/eclampsia, or venous thrombosis such as deep vein thrombosis, venoocclusive disease, haematological conditions such as myeloproliferative disease, including thrombocythaemia, sickle cell disease; or in the prevention of mechanically-induced platelet activation in vivo, such as cardio-pulmonary bypass and extracorporeal membrane oxygenation (prevention of microthromboembolism), mechanically-induced platelet activation in vitro, such as use in the preservation of blood products, e.g. platelet concentrates, or shunt occlusion such as in renal dialysis and plasmapheresis, thrombosis secondary to vascular damage/inflammation such as vasculitis, arteritis, glomerulonephritis, inflammatory bowel disease and organ graft rejection, conditions such as migraine, Raynaud's phenomenon, conditions in which platelets can contribute to the underlying inflammatory disease process in the vascular wall such as atheromatous plaque formation/progression, stenosis/restenosis and in other inflammatory conditions such as asthma, in which platelets and platelet-derived factors are implicated in the immunological disease process.

According to the invention there is further provided the use of a compound according to the invention in the manufacture of a medicament for the treatment of the above disorders. In particular the compounds of the invention are useful for treating myocardial infarction, thrombotic stroke, transient ischaemic attacks, peripheral vascular disease and angina, especially unstable angina. The invention also provides a method of treatment of the above disorders which comprises administering to a patient suffering from such a disorder a therapeutically effective amount of a compound according to the invention.

The compounds may be administered topically, e.g. to the lung and/or the airways, in the form of solutions, suspensions, HFA aerosols and dry powder formulations; or systemically, e.g. by oral administration in the form of tablets, pills, capsules, syrups, powders or granules, or by parenteral administration in the form of sterile parenteral solutions or suspensions, by subcutaneous administration, or by rectal administration in the form of suppositories or transdermally.

The compounds of the invention may be administered on their own or as a pharmaceutical composition comprising the compound of the invention in combination with a pharmaceutically acceptable diluent, adjuvant or carrier. Particularly preferred are compositions not containing material capable of causing an adverse, e.g. an allergic, reaction.

Dry powder formulations and pressurised HFA aerosols of the compounds of the invention may be administered by oral or nasal inhalation. For inhalation the compound is desireably finely divided.

The compounds of the invention may also be administered by means of a dry powder inhaler. The inhaler may be a single or a multi dose inhaler, and may be a breath actuated dry powder inhaler.

One possibility is to mix the finely divided compound with a carrier substance, e.g. a mono-, di- or polysaccharide, a sugar alcohol or another polyol. Suitable carriers include sugars and starch. Alternatively the finely divided compound may be coated by another substance. The powder mixture may also be dispensed into hard gelatine capsules, each containing the desired dose of the active compound.

Another possibility is to process the finely divided powder into spheres which break up during the inhalation procedure. This spheronized powder may be filled into the drug reservoir of a multidose inhaler, e.g. that known as the Turbuhaler® in which a dosing unit meters the desired dose which is then inhaled by the patient. With this system the active compound with or without a carrier substance is delivered to the patient.

The pharmaceutical composition comprising the compound of the invention may conveniently be tablets, pills, capsules, syrups, powders or granules for oral administration; sterile parenteral or subcutaneous solutions, suspensions for parenteral administration or suppositories for rectal administration.

For oral administration the active compound may be admixed with an adjuvant or a carrier, e.g. lactose, saccharose, sorbitol, mannitol, starches such as potato starch, corn starch or amylopectin, cellulose derivatives, a binder such as gelatine or polyvinylpyrrolidone, and a lubricant such as magnesium stearate, calcium stearate, polyethylene glycol, waxes, paraffin, and the like, and then compressed into tablets. If coated tablets are required, the cores, prepared as described above, may be coated with a concentrated sugar solution which may contain e.g. gum arabic, gelatine, talcum, titanium dioxide, and the like. Alternatively, the tablet may be coated with a suitable polymer dissolved either in a readily volatile organic solvent or an aqueous solvent.

For the preparation of soft gelatine capsules, the compound may be admixed with e.g. a vegetable oil or polyethylene glycol. Hard gelatine capsules may contain granules of the compound using either the above mentioned excipients for tablets, e.g. lactose, saccharose, sorbitol, mannitol, starches, cellulose derivatives or gelatine. Also liquid or semisolid formulations of the drug may be filled into hard gelatine capsules.

Liquid preparations for oral application may be in the form of syrups or suspensions, for example solutions containing the compound, the balance being sugar and a mixture of ethanol, water, glycerol and propylene glycol. Optionally such liquid preparations may contain colouring agents, flavouring agents, saccharine and carboxymethylcellulose as a thickening agent or other excipients known to those skilled in art.

The invention is illustrated by the following examples which should not be interpreted as limiting the invention. In the examples the NMR spectra were measured on a Varian Unity Inova 300 or 400 spectrometer and the MS spectra were measured as follows: EI spectra were obtained on a VG 70-250S or Finnigan Mat Incos-XL spectrometer, FAB spectra were obtained on a VG70-250SEQ spectrometer, ESI and APCI spectra were obtained on Finnigan Mat SSQ7000 or a Micromass Platform spectrometer. Preparative HPLC separations were generally performed using a Novapak®, Bondapak®or Hypersil® column packed with BDSC-18 reverse phase silica. Flash chromatography (indicated in the Examples as ($SiO_2$)) was carried out using Fisher Matrix silica, 35–70 µm. For compounds which showed the presence of rotamers in the proton NMR spectrum, only the chemical shifts for the major rotamer are quoted.

EXAMPLE 1

[1S-(1α,3α,4β)]-3-[7-(Butylamino)-5-(propylthio)-3H-1,2,3-triazolo[4,5d]pyrimidin3-yl]-4-hydroxy-cyclopentanecarboxylic Acid a) [1S-(1α,2α,3β,5β)]-5-[7-(Butylamino)-5-(propylthio)-3H-1,2,3-triazolo[4,5-d]pyrimidin-3-yl]-3-(hydroxymethyl)-cyclopentane-1,2-diol A solution of [3aR-(3aα,4α,6α,6aα)]-6-[7-(butylamino)-5-(propylthio)-3H-1,2,3-triazolo[4,5-d]pyrimidin-3-yl]-tetrahydro-2,2-dimethyl-4H-cyclopenta-1,3-dioxole-4-methanol (prepared as described in WO9703084) (5.0 g) in methanol (50 ml) and 1N HCl (50 ml) was stirred at room temperature for 2 hours. Water was added and the product collected by filtration and dried (4.51 g).

MS (APCI) 397 (M+H$^+$)

b) [1R-(1α,2α,4α,5α)]-4-[7-(Butylamino)-5-(propylthio)-3H-1,2,3-triazolo[4,5-d]pyrimidin-3-yl]-6-oxabicyclo[3.1.0]hexane-2-methanol A solution of the product from step (a) (4.3 g) and 2-acetoxy-2-methylpropionyl bromide (7.7 ml) in acetonitrile (200 ml) was stirred overnight at room temperature. The mixture was concentrated and partitioned between ethyl acetate and aqueous sodium bicarbonate. The organic phase was dried, concentrated and the residue dissolved in methanol (500 ml) then Amberlite® IR8(400) OH$^-$ form resin (50 g) added. The mixture was stirred overnight, filtered and concentrated. Purification ($SiO_2$, ethyl acetate: dichloromethane 1:1 as eluant) afforded the subtitle compound (3.2 g).

MS (APCI) 379 (M+H$^+$)

c) [1R-(1α,2α,3β,4α)]-2-Bromo-4-[7-(butylamino)-5-(propylthio)-3H-1,2,3-triazolo[4,5-d]pyrimidin-3-yl]-3-hydroxy-cyclopentanemethanol To a solution of the product from step (b) (3.2 g) in chloroform (20 ml) was added 48% hydrobromic acid (20 ml). The mixture was stirred at room temperature for 15 minutes, concentrated and treated with water (100 ml). The product was collected by filtration (3.3 g).

MS (APCI) 459/461 (M+H+)

d) (1S-1α,3α,4β)-3-[7-(Butylamino)-5-(propylthio)-3H-1,2,3-triazolo[4,5-d]pyrimidin-3-yl]-4-hydroxy-cyclopentanemethanol To a solution of the product from step (c) (0.5 g) in toluene (30 ml) at 80° C. was added tributyltin hydride (0.35 ml) and 2,2'-azobis(2-methylpropionitrile) (10 mg). The mixture was heated at 80° C. for 30 minutes, cooled and the product collected by filtration (0.34 g).

MS (APCI) 381 (M+H+)

e) [1R-(1α,2β,4β)]-4-[[[Bis(4-methoxyphenyl)phenylmethyl]oxy]methyl]-2-[7-(butylamino)-5-(propylthio)-3H-1,2,3-triazolo[4,5-d]pyrimidin-3-yl]-cyclopentan-1-ol A mixture of the product from step (d) (7.1 g), 4,4'-dimethoxytrityl chloride (6.31 g) and 4-dimethylaminopyridine (2.32 g) in dichloromethane (300 ml) was stirred at room temperature for 48 hours and purified (SiO₂, ethyl acetate: dichloromethane 3:97 to 10:90 as eluant) to afford the subtitle compound (10.1 g).

MS (FAB) 683 (M+H+)

f) 3-[[1R-(1α,2β,4α)]-4-[[[Bis(4-methoxyphenyl)phenylmethyl]oxy]methyl]-2[[-(1,1-dimethylethyl)dimethylsilyl]oxy]-cyclopent-1-yl]-N-butyl-5-(propylthio)-3H-1,2,3-triazolo[4,5-d]pyrimidine-7-amine A mixture of the product from step (e) (10.1 g), t-butyldimethylsilyl chloride (2.67 g) and imidazole (1.16 g) in N,N-dimethylformamide (300 ml) was stirred at room temperature for 48 hours, concentrated and purified (SiO₂, ethyl acetate: dichloromethane 5:95 as eluant) to afford the subtitle compound (10.0 g).

MS (EI) 796 (M+)

g) [1S-(1α,3α,4β)]-3-[7-(Butylamino)-5-(propylthio)-3H-1,2,3-triazolo[4,5-d]pyrimidin-3-yl]-4-[[(1,1-dimethylethyl)dimethylsilyl]oxy]-cyclopentanemethanol To a solution of the product from step (f) (10.0 g) in nitromethane/methanol (95:5, 230 ml) was added anhydrous zinc bromide (27.5 g). The mixture was stirred at room temperature for 1 hour and poured into water (1L) containing ammonium acetate (100 g). The product was extracted with ethyl acetate and purified (SiO₂, ethyl acetate: dichloromethane 1:9 as eluant) to afford the subtitle compound (5.6 g).

MS (APCI) 495 (M+H+)

h) [1S-(1α,3α,4β)]-3-[7-(Butylamino)-5-(propylthio)-3H-1,2,3-triazolo[4,5-d]pyrimidin-3-yl]-4-[[(1,1-dimethylethyl)dimethylsilyl]oxy]-cyclopentanecarboxylic Acid A mixture of the product from step (g) (5.5 g) and pyridinium dichromate (55 g) in N,N-dimethylformamide (300 ml) was stirred at room temperature for 7 hours. The mixture was poured into water (1L) and the product collected by filtration and purified (SiO₂, ethyl acetate: dichloromethane 2:8 as eluant) to afford the subtitle compound (4.6 g).

MS (APCI) 509 (M+H+)

i) [1S-(1α,3α,4β)]-3-[7-(Butylamino)-5-(propylthio)-3H-1,2,3-triazolo[4,5-d]pyrimidin-3-yl]-4-hydroxy-cyclopentanecarboxylic Acid To a solution of the product from step (h) (4.3 g) in tetrahydrofuran (100 ml) was added tetrabutylammonium fluoride (20 ml,1M solution in tetrahydrofuran) and the mixture stirred at room temperature overnight. The mixture was poured into water and the product collected by filtration then purified by recrystallisation (ethyl acetate/isohexane) (2.1 g).

MS (APCI) 395 (M+H+)

EXAMPLE 2

[1S-(1α,3α,4β)]-3-[7-(Butylamino)-5-[[4-(trifluoromethyl)phenyl]thio]-3H-1,2,3-triazolo[4,5-d]pyrimidin-3-yl]-4-hydroxy-cyclopentanecarboxylic Acid a) [1S-(1α,3α,4β)]-3-[7-(Butylamino)-5-(propylsulfonyl)-3H-1,2,3-triazolo[4,5-d]pyrimidin-3-yl]-4-hydroxy-cyclopentanecarboxylic Acid To a solution of the product from Example 1, step (i) (0.5 g) in acetonitrile/water (3:2, 100 ml) was added Oxone® (5 g). The mixture was stirred at room temperature for 30 minutes. Water was added and the mixture was extracted with ethyl acetate. The extract was concentrated to afford the product (0.5 g).

MS (APCI) 427 (M+H+)

b) [1S-(1α,3α,4β)]-3-[7-(Butylamino)-5-[[4-(trifluoromethyl)phenyl]thio]-3H-1,2,3-triazolo[4,5-d]pyrimidin-3-yl]-4-hydroxy-cyclopentanecarboxylic Acid To a suspension of sodium hydride (60%, 0.18 g) in N,N-dimethylformamide (30 ml) was added 4-(trifluoromethyl)thiophenol (0.8 g). The mixture was stirred for 30 minutes then the product of step (a) (0.5 g) was added. The mixture was heated at 80° C. for 2 hours, cooled and poured into water. The product was extracted with ethyl acetate and purified (SiO₂, ethanol:dichloromethane 1:9 as eluant). Further purification (HPLC, Novapak® C18 column, 0.1% aqueous ammonium acetate:acetonitrile, gradient elution 40:60 to 0:100 over 15 minutes) afforded the subtitle compound (0.145 g).

MS (APCI) 497 (M+H+)

NMR (d₆-DMSO) 12.29 (1H, s), 9.10 (1H, t), 7.84 (4H, q), 5.29 (1H, d), 4.83 (1H, m), 4.49 (1H, m), 3.19 (2H, m), 3.05 (1H, m), 2.49–2.30 (2H, m), 2.15 (1H, m), 1.95 (1H, m), 1.34 (1H, m), 1.10 (2H, m), 0.78 (3H, t).

EXAMPLE 3

N-[(1S,3R,4S)-3-[7-(Butylamino)-5-[[4-(trifluoromethyl)phenyl]thio]-3H-1,2,3-triazolo[4,5-d]pyrimidin-3-yl]-4-hydroxy-cyclopertylcarbonyl]-L-serine N,N-Diisopropylethylamine (1.0 ml) was added to a solution of L-serine t-butyl ester hydrochloride (0.5 g), bromo-tris-pyrrolidino-phosphonium hexafluorophosphate (1.0 g) and the product of example 2 (0.3 g) in tetrahydrofuran (20 ml). The reaction mixture was stirred at room temperature for 1 hour then poured into water and extracted with ethyl acetate. The extract was concentrated and the residue dissolved in trifluoroacetic acid/dichloromethane (1:1 100 ml). After 1 hour the mixture was concentrated and the residue purified (HPLC, Novapak® C18 column, 0.1% aqueous ammonium acetate:acetonitrile, gradient elution 10:90 to 0:100 over 15 minutes) to afford the title compound (0.17 g).

MS (APCI) 584 (M+H+)

NMR (d₆-DMSO) 9.12 (1H, t), 8.08 (1H, d), 7.83 (4H, q), 5.24 (1H, d), 4.89 (1H, br s) 4.80 (1H m), 4.55 (1H, m), 4.30 (1H, m), 3.65 (2H, m), 3.15 (3H, m),2.34 (2H, m), 2.08 (1H, m), 1.83 (1H, m), 1.34 (1H, m), 1.10 (2H, m), 0.77 (3H, t).

EXAMPLE 4

N-[(1S,3R,4S)-3-[7-(Butylamino)-5-[[4-(trifluoromethyl)phenyl]thio]-3H-1,2,3-triazolo[4,5-d]pyrimidin-3-yl]-4-hydroxy-cyclopentylcarbonyl]-glycine Prepared according to the method of example 2 using the product of example 1 and glycine methyl ester hydrochloride.

MS (APCI) 554 (M+H$^+$)

NMR (d$_6$-DMSO) 9.11 (1H, t), 8.24 (1H, t), 7.55 (4H, q), 5.26 (1H, d), 4.80 (1H, m), 4.55 (1H, m), 3.75 (2H, d), 3.16 (2H, m), 3.01 (1H, m), 2.28 (2H, m), 2.13 (1H, m), 1.81 (1H, m), 1.36 (2H, m), 1.12 (2H, m), 0.77 (3H, t).

EXAMPLE 5

[1S-[1α,3β,4α(1S*,2R*)]]-3-Hydroxy-4-[7[(2-phenylcyclopropyl)amino]-5-(propylthio)-3H-1,2,3-triazolo[4,5-d]pyrimidin-3-yl]-cyclopentanecarboxylic Acid a) [3aR-[3aα,4α,6α(1R*,2S*),6aα]]-Tetrahydro-2,2-dimethyl-6-[7-[(2-phenylcyclopropyl) amino]-5-(propylthio)-3H-1,2,3-triazolo[4,5-d]pyrimidin-3-yl]-4H-cyclopenta-1,3-dioxole-4-methanol N,N-Diisopropylethylamine (21 ml) was added to a solution of [3aR-(3aα,4α,6α,6aα)]-6-[7-chloro-5-(propylthio)-3H-1,2,3-triazolo[4,5-d]pyrimidin-3-yl]-tetrahydro-2,2-dimethyl-4H-cyclopenta-1,3-dioxole-4-methanol (Prepared as described in WO 9703084) (55 g) and (1R-trans)-2-phenyl-cyclopropanamine, [R-(R*,R*)]-2,3-dihydroxybutanedioate (1:1) (prepared as described by L. A. Mitscher et al., J. Med. Chem. 1986, 29, 2044) (11.3 g) in dichloromethane (500 ml). The mixture was stirred at room temperature for 3 hours. The reaction mixture was washed with water, dried and evaporated. The residue was purified (SiO$_2$, ethyl acetate:dichloromethane 3:7 as eluant) to afford the subtitle compound (19 g).

MS (APCI) 497 (M+H$^+$)

b) [1S-[1α,2α,3β,5β(1S*,2R*)]]-3-Hydroxymethyl-5-[7-[(2-phenylcyclopropyl)amino]-5-(propylthio)-3H-1,2,3-triazolo[4,5-d]pyrimidin-3-yl]-cyclopentane-1,2-diol Prepared according to the method of example 1 step (a) using the product of step (a).

MS (APCI) 457 (M+H$^+$)

c) [1R-[1α,2α,4α(1R*,2S*),5α]]-4-[7-[(2-Phenylcyclopropyl)amino]-5-(propylthio)-3H-1,2,3-triazolo[4,5-d]pyrimidin-3-yl]-6-oxabicyclo[3.1.0]hexane-2-methanol Prepared according to the method of example 1 step (b) using the product of step (b).

MS (APCI) 439 (M+H$^+$)

d) [1R-[1α,2α,3β,4α(1R*,2S*)]]-2-Bromo-3-hydroxy-4-[7-[(2-phenylcyclopropyl)amino]-5-(propylthio)-3H-1,2,3-triazolo[4,5-d]pyrimidin-3-yl]-cyclopentanemethanol Prepared according to the method of example 1 step (c) using the product of step (c).

MS (APCI) 519/521 (M+H$^+$)

e) [1S-[1α,3β,4α(1S*,2R*)]]-3-Hydroxy-4-[7-[(2-phenylcyclopropyl)amino]-5-(propylthio)-3H-1,2,3-triazolo[4,5-d]pyrimidin-3-yl]-cyclopentanemethanol Prepared according to the method of example 1 step (d) using the product of step (d).

MS (APCI) 441 (M+H$^+$)

f) [1R-[1α,2β,4β(1R*,2S*)]]-4-[[[Bis(4-methoxyphenyl)phenylmethyl]oxy]methyl]-2-[7-[(2-phenylcyclopropyl)amino]-5-(propylthio)-3H-1,2,3-triazolo[4,5-d]pyrimidin-3-yl]-cyclopentan-1-ol Prepared according to the method of example 1 step (e) using the product of step (e).

MS (APCI) 743 (M+H$^+$)

g) 3-[[1R,2R,4S]-4-[[[Bis(4-methoxyphenyl)phenylmethyl]oxy]methyl]-2-[[(1,1-dimethylethyl)dimethylsilyl]oxy]-cyclopent-1-yl]-N-[[1R-(trans)]-(2-phenylcyclopropyl)amino]-5-(propylthio)-3H-1,2,3-triazolo[4,5-d]pyrimidine-7-amine Prepared according to the method of example 1 step (f) using the product of step (f).

NMR (d$_6$-DMSO) 7.76–7.11 (18H, m), 6.70 (1H, br s), 5.32 (1H, d), 5.04 (1H, m), 4.00 (6H, s), 3.52 (1H, m), 3.42–3.20 (4H, m), 2.92 (1H, m), 2.78 (1H, m), 2.52 (1H, m), 2.42 (1H, m), 2.30–2.10 (2H, m), 1.98 (2H, m), 1.72 (2H, m), 1.20 (3H, t), 1.00 (9H, s), 0.13 (3H, s) 0.00 (3H, s).

h) [1S-[1α,3β,4α(1S*,2R*)]]-3-[[(1,1-Dimethylethyl)dimethylsilyl]oxy]-4-[7-[(2-phenylcyclopropyl)amino]-5-(propylthio)-3H-1,2,3-triazolo[4,5-d]pyrimidin-3-yl]-cyclopentanemethanol Prepared according to the method of example 1 step (g) using the product of step (g).

MS (APCI) 555 (M+H$^+$)

i) [1S-[1α,3β,4α(1S*,2R*)]]-3-[[(1,1-Dimethylethyl)dimethylsilyl]oxy]-4-[7-[(2-phenylcyclopropyl)amino]-5-(propylthio)-3H-1,2,3-triazolo[4,5-d]pyrimidin-3-yl]-cyclopentanecarboxylic Acid Prepared according to the method of example 1 step (h) using the product of step (h).

MS (APCI) 569 (M+H$^+$)

j) [1S-[1α,3β,4α(1S*,2R*)]]-3-Hydroxy-4-[7-[(2-phenylcyclopropyl)amino]-5-(propylthio)-3H-1,2,3-triazolo[4,5-d]pyrimidin-3-yl]-cyclopentanecarboxylic Acid Prepared according to the method of example 1 step (i) using the product of step (i).

MS (APCI) 455 (M+H$^+$)

NMR (d$_6$-DMSO) 12.30 (1H, s), 9.34 (1H, d), 7.31–7.16 (5H, m), 5.32 (1H, d), 4.84 (1H, m), 4.57 (1H, m), 3.20 (1H, m), 3.10 (1H, m), 2.85 (2H, 2x m), 2.48 (2H, m), 2.25 (1H, m), 2.15 (1H, m), 1.95 (1H, m), 1.52 (3H, m), 1.35 (1H, m), 0.81 (3H, t).

EXAMPLE 6

N-[(1S,3R,4S)-3-[7-(Butylamino)-5-(propylthio)-3H-1,2,3-triazolo[4,5-d]pyrimidin-3-yl]-4-hydroxy-cyclopentylcarbonyl]-glycine Prepared according to the method of example 3 using the product of example 1 and glycine tert-butyl ester.

MS (APCI) 450 (M–H$^+$)

NMR (d$_6$-DMSO) 8.99 (1H, t), 8.11 (1H, m), 5.28 (1H, m), 4.86–4.78 (1H, m), 4.60–4.58 (1H, m), 3.50–3.47 (1H, m), 3.70–3.68 (2H, d), 3.16–3.01 (3H, m), 2.41–2.18 (3H, m), 1.90–1.58 (5H, m), 1.40–1.28 (2H, m), 1.01–0.90 (6H, 2x t).

EXAMPLE 7

[1S-(1α,3α,4β)]-3-[7-(Hexylamino)-5-(propylthio)-3H-1,2,3-triazolo[4,5-d]pyrimidin-3-yl]-4-hydroxy-cyclopentanecarboxylic Acid a) [1S-(1α,3α,4β)]-3-[[5-Amino-6-chloro-2-(propylthio)-pyrimidin-4-yl]amino]-4-hydroxy-cyclopentanecarboxylic Acid, methyl ester A solution of [1S-(1α,3α,4β)]-3-amino-4-hydroxy-cyclopentanecarboxylic acid methyl ester hydrochloride (Prepared as described by S. Roberts et al., J.Chem. Soc., Perkin Trans. 1, 1992, 1021) (1.90 g), 4,6-dichloro-5-nitro-2-propylthiopyrimidine (prepared as described in WO9703084) (5.23 g) and triethylamine (6.6 ml) in n-butanol (95 ml) was heated at reflux for 3 hours. The mixture was concentrated and purified (SiO$_2$, diethyl ether: isohexane 1:3 as eluant) to afford the subtitle compound (3.36 g).

MS (APCI) 389 (M–H$^+$,100%)

b) [1S-(1α,3α,4β)]-3-[7-Chloro-2-(propylthio)-3H-1,2,3-triazolo[4,5-d]pyrimidin-3-yl]-4-hydroxy-cyclopentanecarboxylic Acid, methyl ester To a solution of the product from step (a) (2.90 g) in glacial acetic acid (100 ml) was added iron powder (2.1 g). After 2 hours the mixture was neutralised with saturated aqueous sodium bicarbonate and extracted with dichloromethane then concentrated. The intermediate was dissolved in acetonitrile (150 ml) and isoamylnitrite (1.20 ml) added. The solution was heated at 60° C. for 1 hour then evaporated to give the crude subtitle compound (2.82 g).

MS (APCI) 429 (M+H$^+$)

c) [1S-(1α,3α,4β)]-3-[7-(Hexylamino)-5-(propylthio)-3H-1,2,3-triazolo[4,5-d]pyrimidin-3-yl]-4-hydroxy-cyclopentanecarboxylic Acid, methyl ester A solution of the product from step (b) (1.3 g) and n-hexylamine (0.43 ml) in 1,4-dioxane (20 ml) was stirred at room temperature for 20 hours and evaporated to give the subtitle compound (0.90 g).

MS (APCI) 435 (M–H$^+$,100%)

d) [1S-(1α,3α,4β)]-3-[7-(Hexylamino)-5-(propylthio)-3H-1,2,3-triazolo[4,5-d]pyrimidin-3-yl]-4-hydroxy-cyclopentanecarboxylic Acid To a solution of the product from step (c) (0.88 g) in methanol (5 ml) was added a solution of lithium hydroxide monohydrate (0.18 g) in water (20 ml). The mixture was stirred at room temperature for 3 hours and concentrated. Purification (HPLC, Novapak® C18 column, 0.1% aqueous trifluoroacetic acid:methanol, gradient elution 70:30 to 20:80 over 20 minutes) afforded the title compound (0.16 g).

MS (APCI) 423 (M+H$^+$,100%)

NMR (d$_6$-DMSO) 8.99 (1H, t), 5.31 (1H, m), 4.89–4.80 (1H, m), 4.59–4.52 (1H, m), 3.49–3.44 (2H, m), 3.14–3.00 (2H, m), 2.44–2.41 (2H, m), 2.33–2.24 (1H, m), 1.94–1.84 (1H, m), 1.76–1.55 (4H, m), 1.29 (6H, m), 1.06 (3H, t), 0.86 (3H, t).

EXAMPLE 8

[1S-(1α,2β,4α)]-4-[7-(Butylamino)-5-(propylthio)-3H-1,2,3-triazolo[4,5-d]pyrimidin-3-yl]-2-hydroxy-cyclopentanecarboxylic Acid a) [6aR-(6aα,8β,9α,9aβ)]-8-[7-(Butylamino)-5-(propylthio)-3H-1,2,3-triazolo[4,5-d]pyrimidin-3-yl]-hexahydro-2,2,4,4-tetrakis(1-methylethyl)-cyclopenta[f]-1,3,5,2,4-trioxadisilocin-9-ol A mixture of the product from example 1 step (a) (0.3 g), imidazole (0.20 g) and 1,3-dichloro-1,1',3,3'-tetraisopropyldisiloxane (0.26 ml) in N,N-dimethylformamide (5 ml) was stirred at room temperature for 2 hours, concentrated and purified (SiO$_2$, ethyl acetate:dichloromethane 5:95 as eluant) to afford the subtitle compound (0.21 g).

MS (APCI) 639 (M+H$^+$)

b) [6aR-(6aα,8β,9α,9aβ)]-1H-Imidazole-1-carbonothioic Acid O-[8-[7-(butylamino)-5-(propylthio)-3H-1,2,3-triazolo[4,5-d]pyrimidin-3-yl]-hexahydro-2,2,4,4-tetrakis(1-methylethyl)-cyclopenta[f]-1,3,5,2,4-trioxadisilocin-9-yl]ester To a solution of the product from step (a) (3.1 g) in N,N-dimethylformamide was added 1,1'-thiocarbonyldiimidazole (0.95 g). The reaction mixture was heated at 80° C. for 6 hours, concentrated and purified (SiO$_2$, ethyl acetate:dichlomomethane 2:8 as eluant) to afford the subtitle compound (3.4 g).

MS (APCI) 749 (M+H$^+$,100%)

c) [1S-(1α,2β,4α)]-4-[7-(Butylamino)-5-(propylthio)-3H-1,2,3-triazolo[4,5-d]pyrimidin-3-yl]-2-hydroxy-cyclopentanemethanol To a solution of the product from step (b) (3.0 g) in toluene (60 ml) was added AIBN (50 mg) and tributyltin hydride (6.3 ml). The reaction mixture was heated at 80° C. for 1 hour, concentrated and purified (SiO$_2$, ethyl acetate:diichloromethane 5:95 as eluant). The intermediate was dissolved in tetrahydrofuran (50 ml) and treated with tetrabutylammonium fluoride (1.0M solution in tetrahydrofuran, 3 ml). After 2 hours the solution was concentrated and purified (SiO$_2$, methanol: dichloromethane 1:9 as eluant) to afford the subtitle compound (0.98 g).

MS (FAB) 381 (M+H$^+$)

d) [1R-(1α,2β,4β)]-2-[[[Bis(4-methoxyphenyl)phenylmethyl]oxy]methyl]-4-[7-(butylamino)-5-(propylthio)-3H-1,2,3-triazolo[4,5-d]pyrimidin-3-yl]-cyclopentan-1-ol Prepared according to the method of example 1 step (e) using the product from step (c).

MS (FAB) 683 (M+H$^+$)

e) 3-[[1R-(1α,3α,4β)]-3-[[[Bis(4-methoxyphenyl)phenylmethyl]oxy]methyl]-4-[[(1,1-dimethylethyl)dimethylsilyl]oxy]-cyclopent-1-yl]-N-butyl-5-(propylthio)-3H-1,2,3-triazolo[4,5-d]pyrimidine-7-amine Prepared according to the method of example 1 step (f) using the product from step (d).

MS (FAB) 797 (M+H$^+$), 303 (100%).

f) [1S-(1α,2β,4α)]-4-[7-(Butylamino)-5-(propylthio)-3H-1,2,3-triazolo[4,5-d]pyrimidin-3-yl]-2-[[(1,1-dimethylethyl)dimethylsilyl]oxy]-cyclopentanemethanol Prepared according to the method of example 1 step (g) using the product from step (e).

MS (APCI) 495 (M+H$^+$)

g) [1S-(1α,2β,4α)]-4-[7-(Butylamino)-5-(propylthio)-3H-1,2,3-triazolo[4,5-d]pyrimidin-3-yl]-2-[[(1,1-dimethylethyl)dimethyilsilyl]oxy]-cyclopentanecarboxylic Acid, 1,1-dimethylethyl ester Chromium (VI) oxide (0.58 g) was added to a solution of pyridine (0.92 ml) in dichloromethane/N,N-dimethylformamide 4:1 (30 ml) and the mixture was stirred for 15 minutes. To this was added the product from step (f) (0.07 g) followed by acetic anhydride (0.92 ml) and tert-butanol (10.5 ml). The reaction mixture was stirred for 48 hours and poured into water. The product was extracted with dichloromethane and purified (SiO$_2$, methanol: dichloromethane 1:9 as eluant) to afford the subtitle compound (0.45 g).

MS (APCI) 565 (M+H$^+$)

h) [1S-(1α,2β,4α)]-4-[7-(Butylamino)-5-(propylthio)-3H-1,2,3-triazolo[4,5-d]pyrimidin-3-yl]-2-hydroxy-cyclopentanecarboxylic Acid A solution of the product from step (g) (0.44 g) in dichloromethane/trifluoroacetic acid 1:1 (50 ml) was stirred at room temperature for 4 hours, dried and purified (HPLC, Novapak® C18 column, 0.1% aqueous ammonium acetate:methanol, gradient elution 70:30 to 0:100 over 20 minutes) to give the title compound (0.12 g).

MS (APCI) 395 (M+H$^+$)

NMR (d$_6$-DMSO) 9.87 (1H, t), 5.29 (2H, m), 4.54 (1H, m), 3.49 (2H, m), 3.13 (2H, m), 2.76 (1H, m), 2.56 (1H, m), 2.38 (2H, m), 2.16 (1H, m), 1.70 (2H, m), 1.66 (2H, m), 1.56 (2H, m), 0.97 (3H, t), 0.89 (3H, t).

Pharmacological Data

The preparation for the assay of the P$_{2T}$-receptor agonist/antagonist activity in washed human platelets for the compounds of the invention was carried out as follows.

Human venous blood (100 ml) was divided equally between 3 tubes, each containing 3.2% trisodium citrate (4 ml) as anti-coagulant. The tubes were centrifuged for 15 minutes at 240 G to obtain a platelet-rich plasma (PRP) to which 300 ng/ml prostacyclin was added to stabilize the platelets during the washing procedure. Red cell free PRP was obtained by centrifugation for 10 minutes at 125 G followed by further centrifugation for 15 minutes at 640 G. The supernatant was discarded and the platelet pellet resuspended in modified, Calcium Free Tyrode solution (10 ml) (CFT), composition: NaCl 137 mM, NaHCO$_3$ 11.9 mM, NaH$_2$PO$_4$ 0.4 mM, KCl 2.7 mM, MgCl$_2$ 1.1 mM, dextrose 5.6 mM, gassed with 95% O$_2$/5% CO$_2$ and maintained at 37° C. Following addition of a further 300 ng/ml PGI$_2$, the pooled suspension was centrifuged once more for 15 minutes at 640 G. The supernatant was discarded and the platelets resuspended initially in 10 ml CFT with further CFT added to adjust the final platelet count to 2×10$^5$/ml. This final suspension was stored in a 60 ml syringe at 3° C. with air excluded. To allow recovery from PGI$_2$-inhibition of normal function, platelets were used in aggregation studies no sooner than 2 hours after final resuspension.

In all studies, 3 ml aliquots of platelet suspension were added to tubes containing CaCl$_2$ solution (60 μl of 50 mM solution with a final concentration of 1 mM). Human fibrinogen (Sigma, F 4883) and 8-sulphophenyltheophylline (8-SPT which was used to block any P$_1$-agonist activity of compounds) were added to give final concentrations of 0.2 mg/ml (60 μl of 10 mg/ml solution of clottable protein in saline) and 300 nM (10 μl of 15 mM solution in 6% glucose), respectively. Platelets or buffer as appropriate were added in a volume of 150 μl to the individual wells of a 96 well plate. All measurements were made in triplicate in platelets from each donor.

The agonist/antagonist potency was assessed as follows.

Aggregation responses in 96 well plates were measured using the change in absorbance given by the plate reader at 660 nm. Either a Bio-Tec Ceres 900C or a Dynatech MRX were used as the plate reader.

The absorbance of each well in the plate was read at 660 nm to establish a baseline figure. Saline or the appropriate solution of test compound was added to each well in a volume of 10 μl to give a final concentration of 0, 0.01, 0.1, 1, 10 or 100 mM. The plate was then shaken for 5 min on an orbital shaker on setting 10 and the absorbance read at 660 nm. Aggregation at this point was indicative of agonist activity of the test compound. Saline or ADP (30 mM; 10 μl of 450 mM) was then added to each well and the plate shaken for a further 5 min before reading the absorbance again at 660 nm.

Antagonist potency was estimated as a % inhibition of the control ADP response to obtain an IC$_{50}$. Compounds exemplified have pIC$_{50}$ values of greater than 5.0.

What is claimed is:

1. A compound of formula (I)

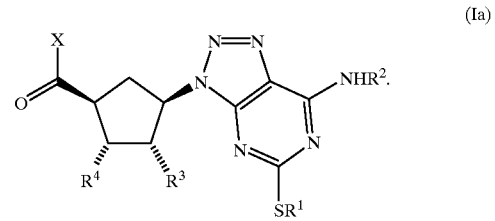

(I)

wherein:
R$^1$ is a C$_{1-6}$ alkyl, C$_{3-8}$-cycloalkyl or a phenyl group, each group being optionally substituted by one or more substituents selected from halogen, OR$^6$, NR$^7$R$^8$, SR$^9$ or C$_{1-6}$ alkyl (itself optionally substituted by one or more halogen atoms);

R$^2$ is C$_{1-8}$ alkyl optionally substituted by one or more substituents selected from halogen, OR$^6$, NR$^7$R$^8$, SR$^9$, C$_{3-8}$-cycloalkyl, aryl (optionally substituted by one or more alkyl groups and/or halogen atoms), or C$_{1-6}$-alkyl; or R$^2$ is a C$_{3-8}$-cycloalkyl group optionally substituted by one or more substituents selected from halogen, OR$^6$, NR$^7$R$^8$, SR$^9$, C$_{1-6}$-alkyl or phenyl (the latter two being optionally substituted by one or more substituents selected from halogen, NO$_2$, C(O)R$^6$, OR$^6$, SR$^9$, NR$^{10}$R$^{11}$, phenyl and C$_{1-6}$-alkyl which is optionally substituted by one or more halogen atoms);

one of R$^3$ or R$^4$ is hydrogen and the other is hydroxy;
X is OH or NHR$^5$;
R$^5$ is a C$_{1-6}$-alkyl group substituted by COOH or C(O)NR$^7$R$^8$ and optionally by one or more further substituents selected from halogen, OR$^{12}$, C(NH)NR$^{13}$R$^{14}$, C(O)NR$^{15}$R$^{16}$ phenyl (optionally substituted by one or more groups selected from halogen, NO$_2$, C(O)R$^6$, OR$^6$, NR$^7$R$^8$, SR$^9$ and C$_{1-6}$-alkyl) or C$_{1-6}$-alkyl (optionally substituted by one or more hydroxy or phenyl groups);
R$^6$, R$^9$, R$^{12}$, R$^{13}$, R$^{14}$, R$^{15}$, and R$^{16}$ are independently hydrogen or C$_{1-6}$-alkyl;
R$^7$ and R$^8$ are independently hydrogen, C$_{1-6}$-alkyl (optionally substituted by one or more phenyl groups) or phenyl groups; and
R$^{10}$ and R$^{11}$ are independently hydrogen, C$_{1-6}$-alkyl or acyl groups;
or a pharmaceutically acceptable salt or solvate thereof.

2. A compound according to claim 1 having the following stereochemistry:

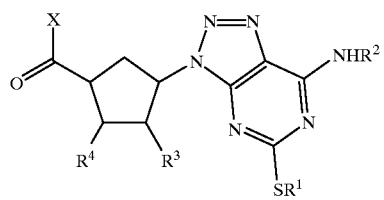

(Ia)

3. A compound according to claim 1 in which R$^1$ is C$_{1-6}$ alkyl or phenyl substituted by C$_{1-6}$ alkyl which is substituted by one or more fluorine atoms.

4. A compound according to claim 1 in which R$^2$ is C$_{1-8}$ alkyl.

5. A compound according to claim 1 in which R$^3$ is hydroxy and R$^4$ is hydrogen.

6. A compound according to claim 1 in which X is OH or NHR$^5$ where R$^5$ is C$_{1-6}$-alkyl substituted by COOH and optionally further substituted by C$_{1-6}$-alkyl substituted by OH.

7. A compound according to claim 1 which is:
[1S-(1α,3α,4β)]-3-[7-(Butylamino)-5-(propylthio)-3H-1,2,3-triazolo[4,5-d]pyrimidin-3-yl]-4-hydroxy-cyclopentanecarboxylic acid,
[1S-(1α,3α,4β)]-3-[7-(Butylamino)-5-[[4-(trifluoromethyl)phenyl]thio]-3H-1,2,3-triazolo[4,5-d]pyrimidin-3-yl]-4-hydroxy-cyclopentanecarboxylic acid,
N-[(1S,3R,4S)-3-[7-(Butylamino)-5-[[4-(trifluoromethyl)phenyl]thio]-3H-1,2,3-triazolo[4,5-d]pyrimidin-3-yl]-4-hydroxy-cyclopentylcarbonyl]-L-serine,
N-[(1S,3R,4S)-3-[7-(Butylamino)-5-[[4-(trifluoromethyl)phenyl]thio]-3H-1,2,3-triazolo[4,5-d]pyrimidin-3-yl]-4-hydroxy-cyclopentylcarbonyl]-glycine,

[1S-[1α,3β,4α(1S*,2R*)]]-3-Hydroxy-4-[7-[(2-phenylcyclopropyl)amino]-5(propylthio)-3H-1,2,3-triazolo[4,5-d]pyrimidin-3-yl]-cyclopentanecarboxylic acid, N-[(1S,3R,4S)-3-[7-(Butylamino)-5-(propylthio)-3H-1,2,3-triazolo[4,5-d]pyrimidin-3-yl]-4-hydroxy-cyclopentylcarbonyl]-glycine,

[1S-(1α,3α,4β)]-3-[7-(Hexylamino)-5-(propylthio)-3H-1,2,3-triazolo[4,5-d]pyrimidin-3-yl]-4-hydroxy-cyclopentanecarboxylic acid,

[1S-(1α,2β,4α)]-4-[7-(Butylamino)-5-(propylthio)-3H-1,2,3-triazolo[4,5-d]pyrimidin-3-yl]-2-hydroxy-cyclopentanecarboxylic acid, and pharmaceutically acceptable salts thereof.

8. A pharmaceutical composition comprising a compound according to claim 1 in combination with a pharmaceutically acceptable diluent, adjuvent or carrier.

9. A process for the preparation of a compound of formula according to claim 1 (I) which comprises oxidising a compound of formula (II):

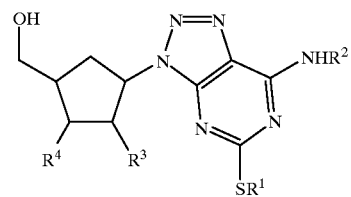

where $R^1$, $R^2$, $R^3$ and $R^4$ are as defined in formula (I) or are protected derivatives thereof, and optionally thereafter in any order:
converting a compound of formula (I) into a further compound of formula (I)
removing any protecting groups
forming a pharmaceutically acceptable salt or solvate.

10. A method of treatment of a platelet aggregation disorder which comprises administering to a patient suffering from such a disorder a therapeutically effective amount of a compound according to claim 1.

11. A method of treatment of angina which comprises administering to a patient suffering from angina a therapeutically effective amount of a compound according to claim 1.

* * * * *